(12) United States Patent
Veloz et al.

(10) Patent No.: US 9,666,424 B1
(45) Date of Patent: May 30, 2017

(54) METHOD AND APPARATUS FOR OPERATING A GERMICIDAL UV DEVICE WITH A PROGRAMMABLE LOGIC CONTROLLER AND A BLUETOOTH LOW ENERGY SOLUTION

(71) Applicants: Peter Veloz, Glendale, CA (US); Ashish Mathur, Santa Clarita, CA (US); Aleksandr Shostak, Northridge, CA (US); Richard Hayes, Thousand Oaks, CA (US); David Witham, Ventura, CA (US); Mitch Babkes, Santa Clarita, CA (US); Filiberto Betancourt, North Hills, CA (US); Lev Rotkop, Beverly Hills, CA (US); Stuart Tyrrell, Los Altos, CA (US); Walt Maclay, Sunnyvale, CA (US); Dan Brown, San Jose, CA (US)

(72) Inventors: Peter Veloz, Glendale, CA (US); Ashish Mathur, Santa Clarita, CA (US); Aleksandr Shostak, Northridge, CA (US); Richard Hayes, Thousand Oaks, CA (US); David Witham, Ventura, CA (US); Mitch Babkes, Santa Clarita, CA (US); Filiberto Betancourt, North Hills, CA (US); Lev Rotkop, Beverly Hills, CA (US); Stuart Tyrrell, Los Altos, CA (US); Walt Maclay, Sunnyvale, CA (US); Dan Brown, San Jose, CA (US)

(73) Assignee: ULTRAVIOLET DEVICES, INC., Valencia, CA (US)

( * ) Notice: Subject to any disclaimer, the term of this patent is extended or adjusted under 35 U.S.C. 154(b) by 0 days.

(21) Appl. No.: 15/044,103

(22) Filed: Feb. 15, 2016

Related U.S. Application Data

(63) Continuation-in-part of application No. 14/325,357, filed on Jul. 7, 2014, now Pat. No. 9,265,174.

(60) Provisional application No. 62/220,932, filed on Sep. 18, 2015.

(51) Int. Cl.
| | | |
|---|---|---|
| *A61L 2/10* | (2006.01) | |
| *A61L 9/20* | (2006.01) | |
| *H05K 7/20* | (2006.01) | |
| *H01J 61/52* | (2006.01) | |
| *H04W 4/00* | (2009.01) | |

(52) U.S. Cl.
CPC ............... *H01J 61/52* (2013.01); *A61L 2/10* (2013.01); *A61L 9/20* (2013.01); *H04W 4/008* (2013.01)

(58) Field of Classification Search
CPC . A61L 2/00; A61L 2/0029; A61L 2/08; A61L 2/10
USPC ..... 250/493.1, 494.1, 504 R, 504 H; 422/20, 422/21, 22, 24
See application file for complete search history.

(56) References Cited

U.S. PATENT DOCUMENTS

2012/0305787 A1* 12/2012 Henson ..................... A61L 2/10
                                                             250/372

* cited by examiner

*Primary Examiner* — Nicole Ippolito
(74) *Attorney, Agent, or Firm* — Law Office of David Hong

(57) ABSTRACT

This invention employs a programmable logic controller (computer) with a specific wireless communication protocol (BLE) to allow for remote connectivity of the germicidal UV device to display the status of the disinfection cycle and to operate the device and send and transfer data wirelessly to the Cloud via the BLE interface.

8 Claims, 19 Drawing Sheets

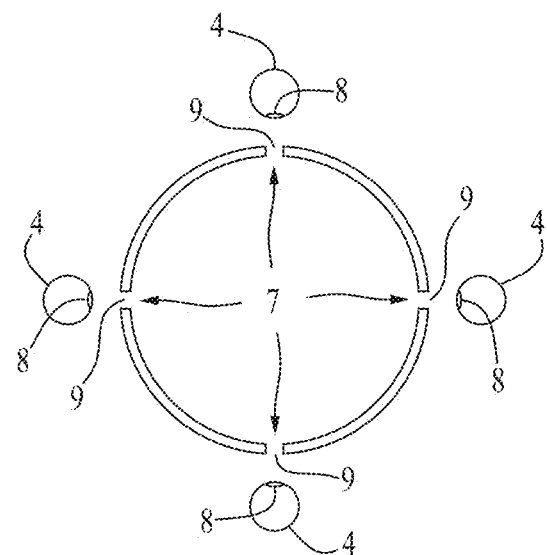
fig. 3A
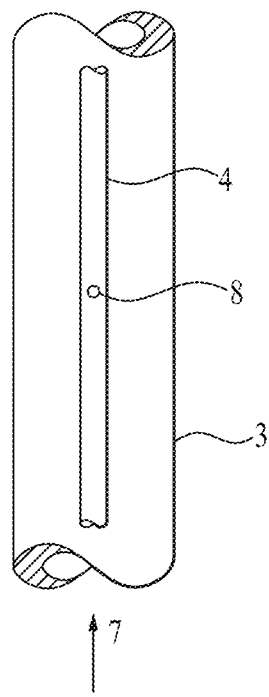 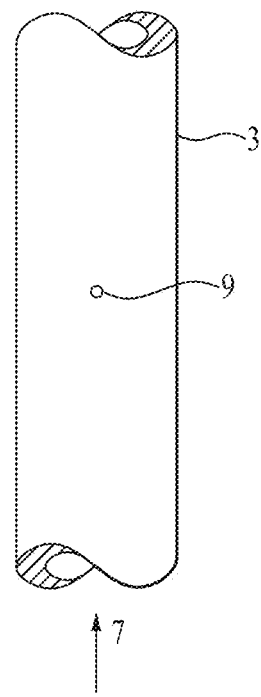
fig. 3B  fig. 3C

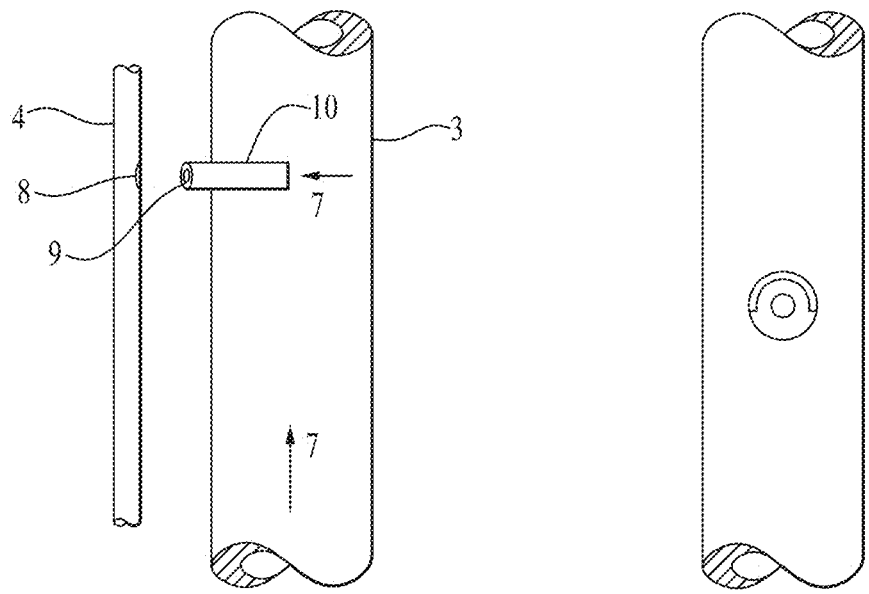
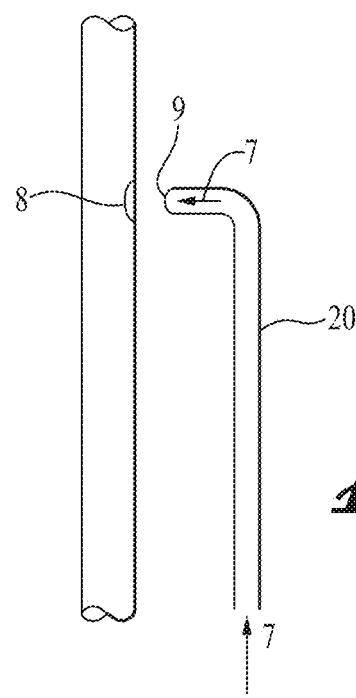

An overview of the architecture is as follows:

METHOD AND APPARATUS FOR OPERATING A GERMICIDAL UV DEVICE WITH A PROGRAMMABLE LOGIC CONTROLLER AND A BLUETOOTH LOW ENERGY SOLUTION

PRIORITY CLAIM

This application is a continuation in part of U.S. patent application Ser. No. 14/325,357, filed on Jul. 7, 2014, and issued as U.S. Pat. No. 9,265,174 on Feb. 16, 2016, which claims the benefit of U.S. Provisional Patent Appl. No. 61/895,010, filed on Oct. 24, 2013; this application also claims the benefit of U.S. Provisional Patent Appl. No. 62/220,932, filed on Sep. 18, 2015; this application is also related to U.S. Design Pat. No. D684,671, which was issued on Jun. 19, 2013; all mentioned applications and patents are incorporated by reference in entirety.

BACKGROUND OF THE INVENTION

The effectiveness of germicidal ultraviolet (UV-C) irradiation as a powerful disinfecting technology has been well documented in peer-reviewed literature as well as in practice. Germicidal UV-C disinfection has been used for decades in disinfecting municipal drinking water, waste water, and in air and surface applications to disinfect against various micro-organisms such as bacteria, virus and mold. UVC devices employ one or more lamps emitting a spectral wavelength output of approximately 254 nm which disrupts the DNA structure of the micro-organisms, rendering them harmless and unable to reproduce.

The lamps typically used in these devices are low pressure mercury vapor discharge lamps. There are three basic types of low pressure ultraviolet lamps in commercial use. A standard output lamp, with input of approximately 425 milliamps has been used for many years. For about two decades, a higher output type lamp with an input of about 850 milliamps has been utilized. Recently a very high output lamp with an input current of from 2.0 to as high as 8.0 amps has become popular in some types of disinfection application. Applications of this type of lamp are popular where high levels of UVC are required such as in municipal water treatment plants.

Construction of the lamp and the materials used are somewhat different to accommodate the high temperatures. With the standard and high output lamps, pure mercury is generally used in the lamp to generate the UVC wavelength of approximately 254 nm. In the very high output lamp, generally the mercury is supplied in an amalgam of metals and may be located on one or more spots placed on the inside of the lamp envelope.

The necessary relatively high doses of ultraviolet radiation typically required to achieve desired disinfection levels requires the use of multiple germicidal lamps. The use of multiple germicidal lamps increases expenses, as well as maintenance. Therefore, it is desirable to use fewer very high output germicidal lamps.

However, applying a very high output germicidal lamp, particularly in air, is not without difficulties. During operation of a low pressure mercury vapor discharge lamp, the vapor pressure of the mercury greatly affects lamp output. For an efficient operation of the lamp, a predetermined range of the mercury vapor pressure inside the discharge vessel is required.

By using an amalgam containing mercury, the mercury vapor pressure can be controlled within this predetermined range for a relatively broad temperature range, allowing operating the lamp at a high efficiency and to deliver a relatively high radiation output within this temperature range. Very high output amalgam lamps thus provide the highest UVC output amongst low pressure mercury lamps and are therefore highly desirable for use for disinfection applications.

The mercury or amalgam of mercury may be located in many different places. In many lamps, it is typically located in one or more locations of the glass inner surface facing the discharge space of the low-pressure mercury vapor discharge lamp. As a result, the amalgam is exposed directly to the discharge space so that the temperature of the amalgam can increase relatively rapidly after the discharge lamp is turned on or lit up. The ideal operating temperature range for germicidal amalgam lamps can vary due to the composition of the amalgam. Typically, it is from 80 degrees C. to 140 degrees C.

However, the higher temperatures occurring at high loading of the lamp may cause the temperature of the amalgam to exceed the maximum operating temperature. This high temperature is not generally a problem when very high output lamps are used for water treatment. In this application, the lamps are generally housed in a quartz sleeve and submerged in moving water, which allows cooling of the lamp and maintains the temperature within the proper temperature range. This is most likely the reason that most applications of very high output lamps are limited to water treatment applications only.

Currently, there are little or no applications of very high output lamps in ambient air. In this air application, the temperature at the amalgam spot can exceed 150 degrees C. If the amalgam melts, several things may happen. The amalgam may move out of position and could make contact with an electrode and cause possible shorting or ineffective operation of the lamp. The molten amalgam material may be spread throughout the lamp and solidify at those positions when the operating conditions change. Solidified amalgam material at a position within the discharge path, for example, may become too hot at a later stage of the lamp use, i.e. the amalgam temperature will become outside its temperature range. When the amalgam is operating outside its ideal temperature range, this results in too high a mercury vapor pressure and hence reduces the lamp efficiency.

The positioning of the (germicidal) lamp, i.e. horizontal versus vertical positioning of the lamp, also influences the temperature of the amalgam. If the system design and application do not allow the amalgam to get into their proper operating temperature range, the lamp will have very low UV output and tend to be quite unstable.

Amalgam lamps provide the highest UVC output amongst low pressure mercury lamps and are therefore highly desirable for use in disinfection applications. However, due to the susceptibility of the amalgam to melt when the temperature exceeds the operating range, the use of germicidal amalgam lamps has been almost exclusively limited to water or liquid disinfection applications, wherein the amalgam lamps are constantly submerged in water or liquids, allowing the lamps to operate in the ideal temperature range.

It is the purpose of this invention to solve these temperature problems for air and surface disinfection applications.

SUMMARY OF THE INVENTION

It is highly desirable to be able to utilize germicidal lamps and in particular very high output germicidal lamps for air and surface applications. The present invention discusses a novel approach to utilize the very high UVC output of germicidal amalgam lamps in UVC disinfection devices in air and surface applications by providing a means to reduce and/or control the temperature of the amalgam spot(s) thus allowing the lamp to operate in its ideal operating range.

In another embodiment of the application, there is a PLC with BLE hardware and software solution that can be integrated with the PLC and HMI system on the UV device in order to communicate with the UV device wirelessly and transmit the data to a controlled Cloud based server.

Another object of this invention is to allow the use of the germicidal amalgam lamp for use in a vertical configuration in a UVC disinfection device by ensuring that the amalgam is kept in its position and operating within the ideal temperature range. Yet another object of this invention is to reduce or eliminate the possibility of the amalgam melting. The present invention allows the germicidal amalgam lamps to be used in devices for air and surface disinfection where the amalgam lamp is exposed to ambient air. The invention discloses a novel approach to cool and/or control the temperature of the amalgam spot, thereby preventing the amalgam spot from melting and allowing the lamp to operate in an ideal operating temperature range and deliver maximum UVC output.

An example of a UVC disinfection device is the V-360+ mobile disinfection device, by UltraViolet Devices, Inc., which is used to disinfect surfaces in a healthcare environment. It is therefore highly desirable to utilize amalgam lamps to maximize the UVC output of the V360+ device and allow rapid disinfection times. The V-360+ device (See FIG. 1) utilizes more than one or four germicidal amalgam lamps which are located around a highly reflective hollow cylindrical aluminum support/conduit mounted at the center of a circular base. The combination of the high output amalgam lamps and the highly reflective support allows the V360+ device to deliver a high dose of UVC in order to achieve high levels of disinfections and rapid disinfection times.

However, with the lamps positioned in a vertical configuration, the amalgam spots are highly susceptible to overheating and even melting and moving out of position due to conditions described previously.

When the device is used in a typical ambient environment, the temperature of the critical spots (amalgam) can exceed 150 degrees C. and make the lamp operate outside its ideal operating range. The proximity of these lamps to the aluminum support lends to even higher temperature at the amalgam spot or spots.

This invention overcomes this challenge by providing an effective method to control the temperature of the critical spot(s) of the lamps on this device. In one embodiment of the application, the temperature of the critical spot (amalgam) is maintained by directing a uniform flow of air on and around the critical spot or spots (amalgam). The flow of air is generated by a fan located inside the V-360+, whereby the flow of air is directed to the critical spot (amalgam) through apertures located on the cylindrical conduit in close proximity to the spot or spots. The size of the cooling fan, location on the cylindrical conduit and the size of the apertures are judiciously chosen to provide an optimal amount of air flow through the apertures on the cylindrical conduit.

The air flow obtained through this arrangement is such that it provides an optimal amount of cooling in order maintain the temperature of the amalgam spot or spots in the ideal operating range, approximately between 80 deg C. and 140 deg C.

In another embodiment of the application, air flow is provided to the amalgam spot or spots through the use of air distribution nozzles that are mounted on the support and/or conduit in close proximity to the critical spot or spots, wherein the air flow is generated by the fan located optimally inside the device.

In another embodiment of the application, air flow is provided to the amalgam spot(s) via air diverter tubes that are mounted inside the support/conduit in close proximity to the amalgam spot or spots and divert an optimal amount of air onto the amalgam spot or spots.

In another embodiment of the application, the temperature of the critical spot or points is controlled by the use of a heat sink that is mounted on the critical spot or points and is connected to the support. By transferring the excess heat to the support, the heat sink maintains the temperature of the critical spot or spots (amalgam) in the desired operating range.

In yet another embodiment, a thermoelectric device is affixed to the critical spots (amalgam) of the lamp and is used to control the temperature of the critical spot. The thermoelectric device may be controlled to maintain a pre-determined temperature, within the ideal temperature range. A temperature sensing device may also be used by the controller.

BRIEF DESCRIPTION OF THE DRAWINGS

FIG. 3a. A horizontal cross sectional view of the device shown in FIG. 1 (enlarged).

FIG. 3b. An enlarged portion of the conduit 3, shown in FIG. 2.

FIG. 3c. The view shown in FIG. 3b with the lamp 8 removed for clarity.

FIG. 4a. A view of an alternate embodiment showing use of an additional component to direct air.

FIG. 4b. A view of the additional component of FIG. 4a from inside the conduit 3.

FIG. 4c. A view of an individual conduit (alternate embodiment)

DETAILED DESCRIPTION OF THE INVENTION

Figure 1:
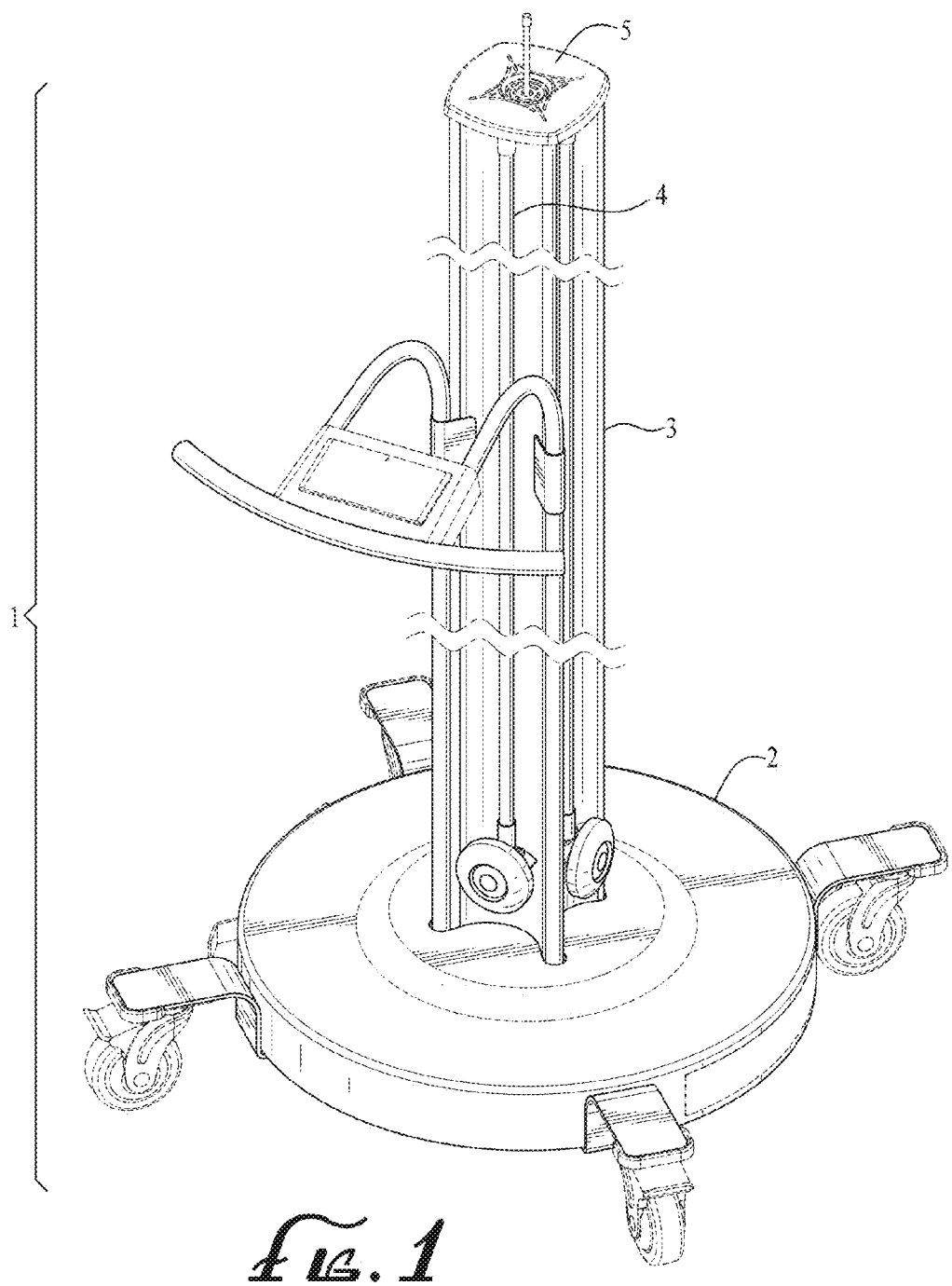
FIG. 1. An isometric drawing of one preferred embodiment of the UVC device utilizing this invention.

Referring to FIG. 1, a typical device 1 for the UV disinfection of air or surfaces is shown. The basic elements of the device are a base 2, a support, in this case, acting also as a conduit 3 and an opening 5 for the exit of air. One or more lamps 4 are installed around the support or conduit 3.

Figure 2:
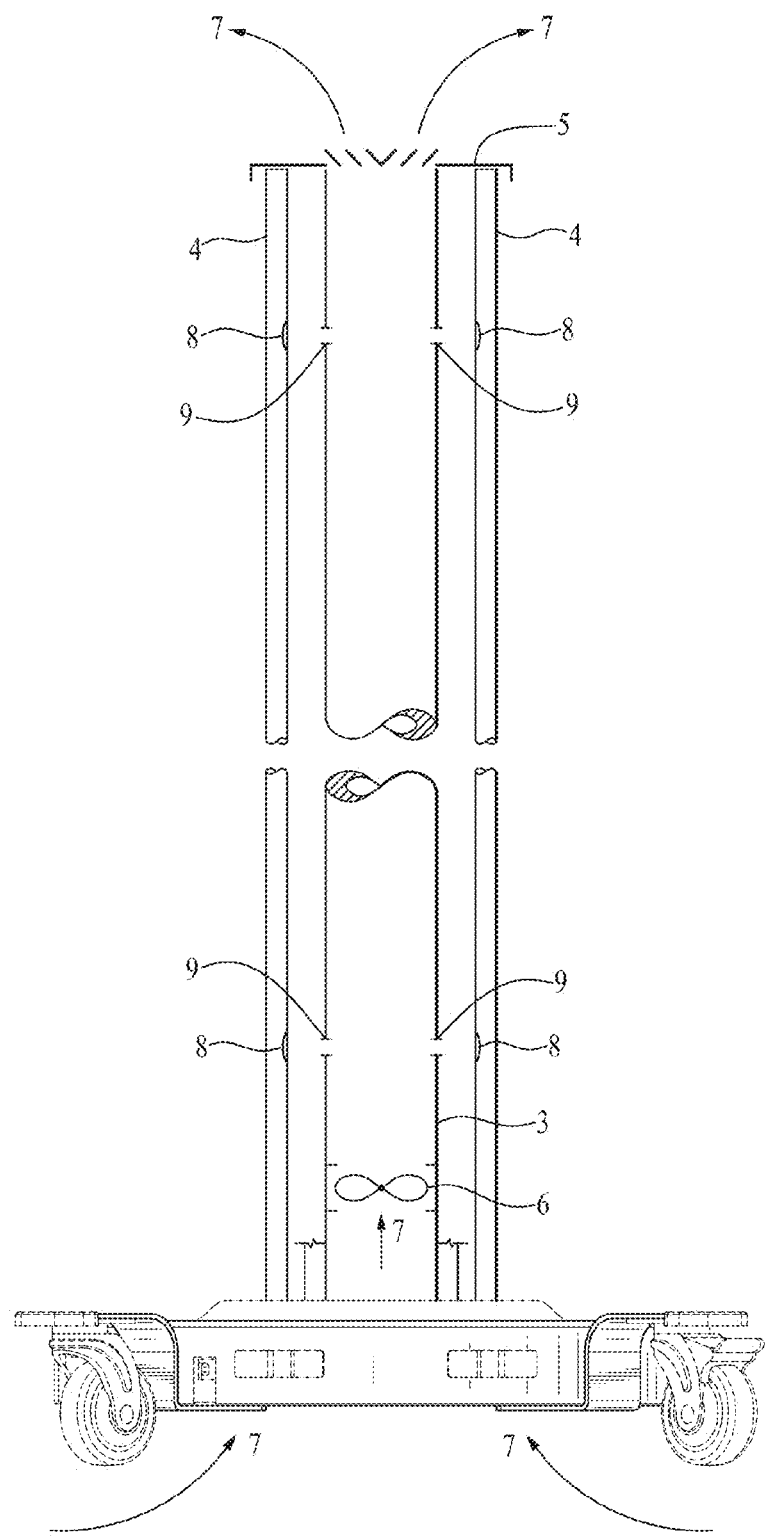
FIG. 2. A vertical cross sectional view of the device shown in FIG. 1

FIG. 2 shows the typical device 1, in cross section. An air moving device 6, including without limitation a fan or blower, is installed in the conduit 6 or may be installed in the base 2. The air moving device 6 causes air 7 to move into the conduit 3 and much of the air to exit through opening 5. Orifices, openings or holes 9 of a specific pre-determined diameter are placed in the conduit 4 at a strategic point selected to direct the air 7 through the orifices 9 to an area near or at the critical spot or points 8 (including mercury spot or amalgam spot, which contains mercury) on the lamp 4.

In another embodiment, not shown, the opening 5 may be omitted allowing all the air 7 to be directed through the orifices 9. In yet another embodiment (not shown), a multitude of small conduits could be used to individually supply air 7 to orifices 9.

FIG. 3a shows a horizontal cross sectional view through the conduit 3. Air 7 flows through the orifices 9 and is directed to the critical spot 8 on the lamp 4. FIG. 3b shows a portion of the conduit 3 with the lamp 4. In FIG. 3c, the lamp 4 is removed to better show one of the orifices 9.

An alternate embodiment of this invention is shown in FIG. 4a which shows a portion of the conduit 3 with a diverter or nozzle 10 installed in the conduit 3 to improve air flow to the critical spot 8. The nozzle/diverter 10 contains the proper size orifice 9. FIG. 4b shows a view of the nozzle/diverter 10 from inside the conduit. An alternate embodiment for delivering cooling air 7 to the critical spot 8 is shown in FIG. 4c and it consists of one or more individual conduits 20 for each critical spot 8.

Figure 5:
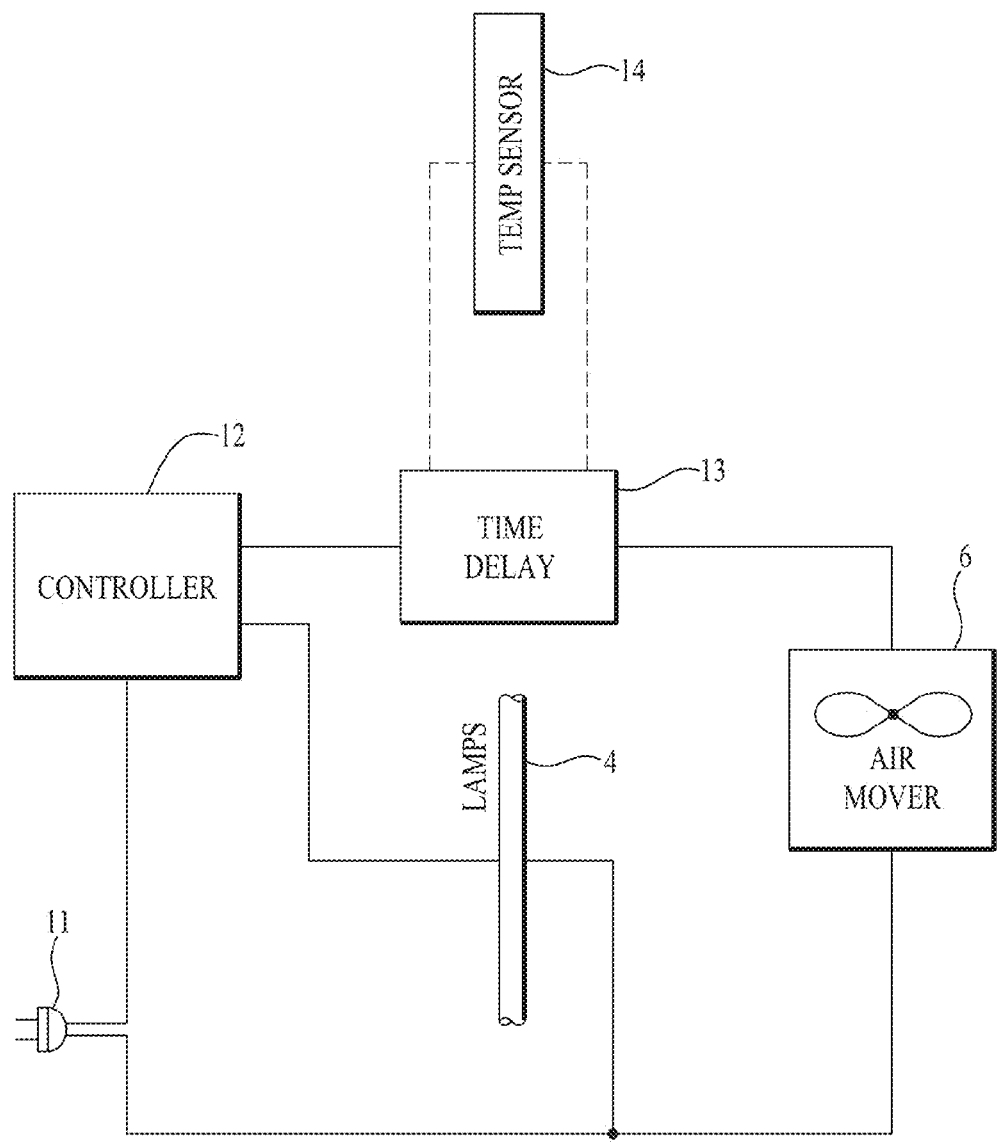
FIG. 5. A schematic showing a control circuit for controlling operation of the air moving component.

Often, it is advantageous to allow the lamp to come up to the proper temperature rapidly prior to applying cooling air 7. A means (a part of this invention) is shown to delay operation of the air moving device 6 is shown in FIG. 5; a delay operation is useful to allow the UV lamp to reach a preferred operating temperature. Alternatively, this may also power a thermo electric cooling device 17. A source of power 11 powers a main controller 12, which normally operates the lamps 4 and the air mover 6, as appropriate. A hardware or software time delay 13 is located in the control circuit, such that operation of the air mover 6 can be controlled or delayed. Optionally, a temperature sensor 14 may be added to the time delay 13 or controller 12 to control operation of the air mover 6.

Figures 6, 7:
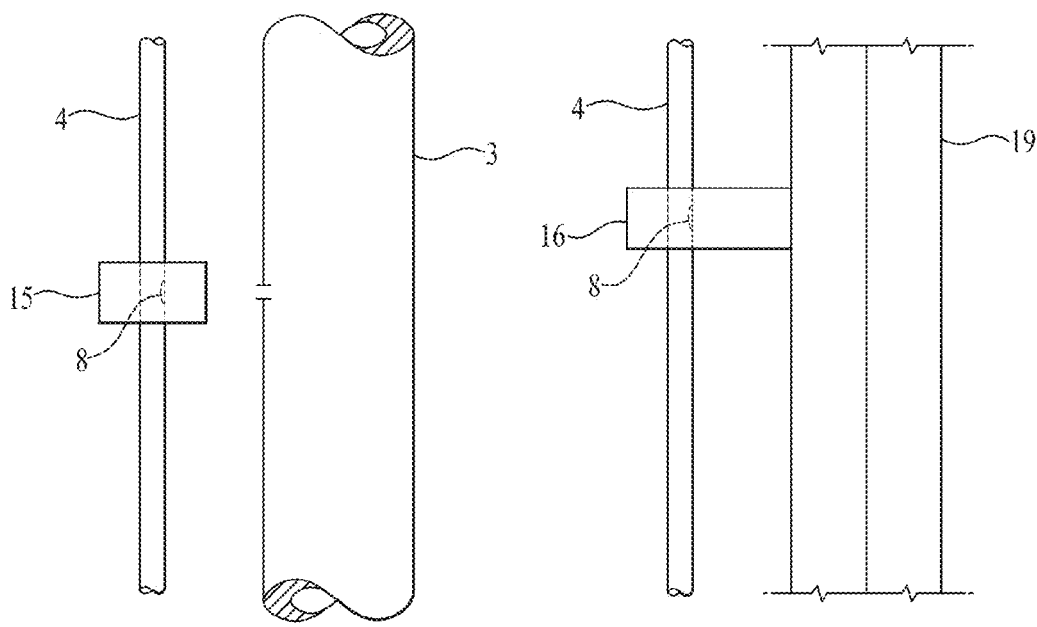
FIG. 6. A side view of an alternate embodiment incorporating heat sinks attached to the UV lamp.
FIG. 7. A side view of an alternate embodiment with a heat sink attached to the UV lamp and in contact with a structural member.

Alternate methods (another part of this invention) to remove heat from the critical spots 8 of the lamp 4 are shown in FIGS. 6 and 7. A heat sink collar 15 may be applied to the lamp 4 around the critical spot 8. Heat is transferred from the critical spot 8 to the ambient air. The heat sink 15 may or may not be additionally cooled with air from the orifices 9. In another embodiment, the heat sink 16 is larger and contacts a support 19 in the apparatus to further draw heat from the critical spot 8.

Figure 8:
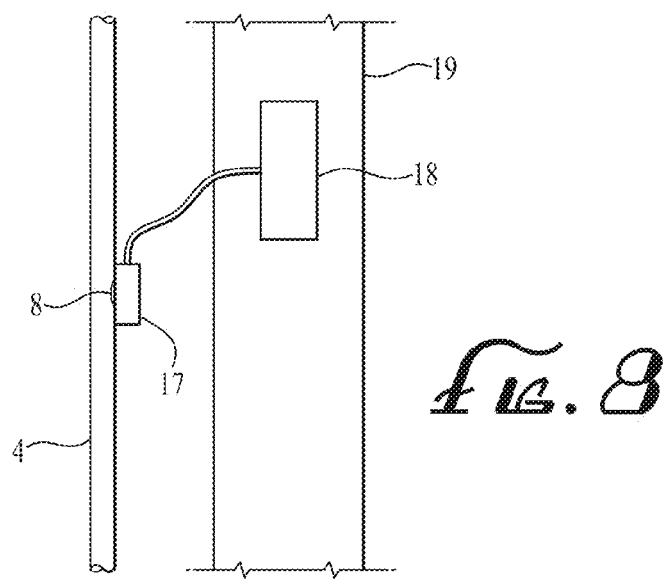
FIG. 8. A view of a solid state thermoelectric device attached to the UVC lamp.

In yet another embodiment of the invention, shown in FIG. 8, a thermoelectric cooling/heating device 17 is used to control the temperature of the critical spots 8. The temperature of the thermoelectric heating/cooling device 17 and the heat controlling capacity may be controlled by a controller 18.

An apparatus for disinfection of air and surfaces, comprising:
A UV lamp having a mercury amalgam spot;
A power source;
A conduit body, which has at least one hole that is located near the mercury spot of the UV lamp; and An air moving device, which delivers air through the at least one hole in the conduit body and near the mercury spot of the UV lamp, Whereby the air moving device provides cooling to alter temperature near the mercury amalgam spot of the UV lamp.

The apparatus further comprises at least one hole is an air director, which is located near the mercury amalgam spot of the UV lamp; a controller is used to modulate speed of the air moving device in order to maintain the temperature of the UV lamp; the controller uses a temperature sensor located near the mercury amalgam spot to maintain the temperature of the UV lamp; the mercury amalgam spot comprises, mercury or an amalgam; the air moving device keeps the mercury amalgam spot below its melting temperature; the air moving device keeps the mercury amalgam spot between 80 degrees C. and 150 degrees C.; the air director is a nozzle, an orifice or a diverter; the controller has a delay function to delay operation of the air moving device, in order to allow the UV lamp to reach an operating temperature.

An apparatus for disinfection of air and surfaces, comprising:
A UV lamp having a mercury amalgam spot;
A power source;
A thermo-electric device, which is in contact with the UV lamp near the mercury amalgam spot, whereby the thermo-electric device allows for heating or cooling to the mercury amalgam spot of the UV lamp.

The apparatus further comprising the thermo-electric device uses a temperature sensor located near the mercury amalgam spot of the UV lamp; the mercury amalgam spot comprises, mercury or an amalgam; the thermo-electric device keeps the mercury amalgam spot below its melting temperature; the thermo-electric device keeps the mercury amalgam spot between 80 degrees C. and 150 degrees C.; there is an air moving device, which directs air through at least one hole near the mercury amalgam spot of the UV lamp.

An apparatus for disinfection of air and surfaces, comprising:
A UV lamp having a mercury amalgam spot;
A power source; and
A heat sink, which is in contact with the UV lamp near the mercury amalgam spot, whereby the heat sink allows for heat dissipation from the UV lamp.

The apparatus further comprising: the heat sink is connected to an adjacent structural component of the apparatus to increase the heat dissipation from the UV lamp; the mercury amalgam spot comprises, mercury or an amalgam; the heat sink keeps the mercury amalgam spot below its melting temperature; the heat sink keeps the mercury amalgam spot between 80 deg. C. and 150 deg. C.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Further, the title, headings, terms and phrases used herein are not intended to limit the subject matter or scope; but rather, to provide an understandable description of the invention. The invention is composed of several sub-parts that serve a portion of the total functionality of the invention independently and contribute to system level functionality when combined with other parts of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Any element in a claim that does not explicitly state "means for" performing a specific function, or "step for" performing a specific function, is not be interpreted as a "means" or "step" clause as specified in 35 U.S.C. Sec. 112, Paragraph 6. In particular, the use of "step of" in the claims herein is not intended to invoke the provisions of 35 U.S.C. Sec. 112, Paragraph 6.

Incorporation by Reference: All publications, patents, and patent applications mentioned in this specification are herein incorporated by reference to the same extent as if each individual publication, patent, or patent application was specifically and individually indicated to be incorporated by reference, including: US 2012/0305787A1 (Henson); U.S. Pat. No. 8,575,567B2 (Lyslo); U.S. Pat. No. 7,658,891B1 (Barnes); US 2005/0258378A1 (Speer).

PLC & BLE:

UVDI's V-360 and V-360 Plus portable UV disinfection sanitizer product family employ a PLC (programmable logic controller) to control its operation and has a HMI (human machine interface) on the device for its user interface. One embodiment of using the invention includes: moving the UV device to a room, manually entering a specific time for a disinfection cycle on the HMI and leaving the room (to prevent exposure from UV radiation) until the cycle is complete. Motion sensors on the device prevent operation if people are present or enter the room during a cycle. The UV device is then moved to another location, and the process repeated. The device captures data such as date and time of operation, user name, room number, disinfection time, performance status etc. This data is currently stored on the PLC/HMI system locally and can be downloaded through a cabled connection to a supplied tablet that is provided with the UV device.

UVDI is currently working on the next generation of the device and plans to include some additional features, including without limitation: wireless connectivity to/from the UV Disinfection Device. This invention presents one preferred embodiment of the hardware and firmware solution that can be integrated with the PCL/HMI system on the UV device in order to communicate with the UV device wirelessly and transmit the data file to a UVDI controlled Cloud based server.

The main problem with existing PCL/HMI systems is that there was no way to communicate between a PLC using a wireless technology like BLE or Bluetooth Low Energy. BLE is preferred since most existing smartphones and other mobile computing devices have a built-in capability to communicate using small packets of encrypted data via BLE. To resolve this problem of communication between the mobile computing device (i.e. table or smartphone) and the UV device's PLC, there is presented a hardware and software module on the UV device, which allows access to the operating status of the device and the transfer of data (typically a .csv file) for further processing. Wireless connectivity is to be provided via BLE. Via BLE, the data should be able to be transmitted to a smart device (tablet or phone), which is enabled by a software application or mobile app. This app will serve as a gateway to view and move the data file to a Cloud based server from the smart device.

Figure 9:
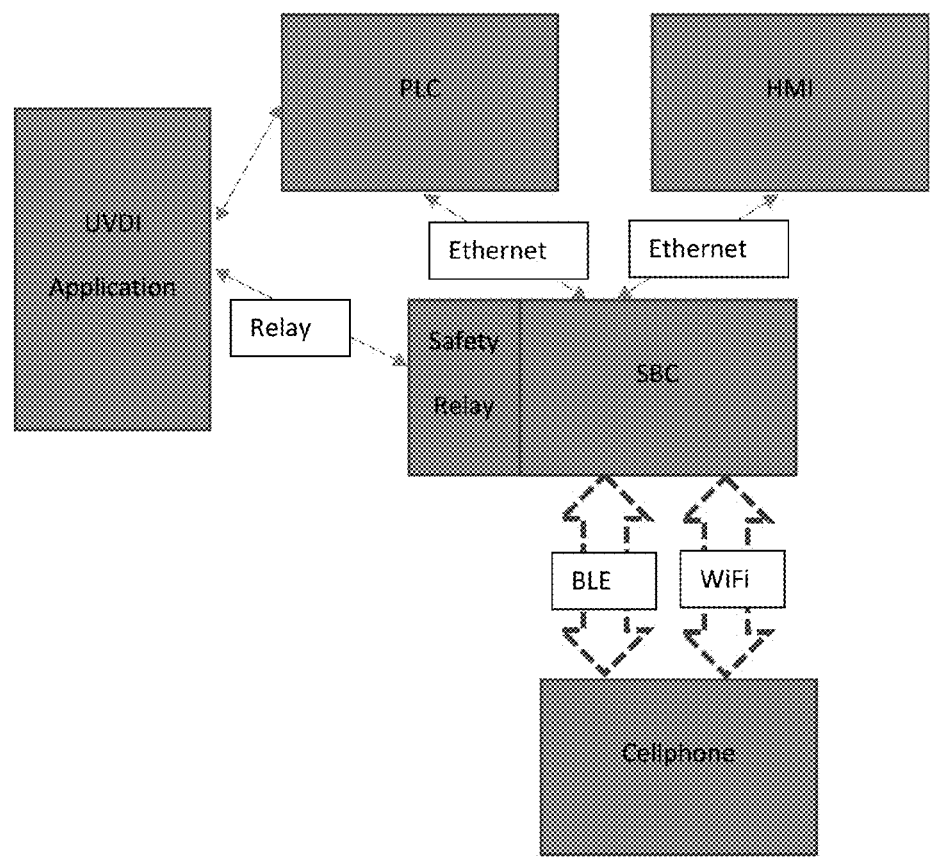
FIG. 9. An overview of the architecture of the PLC and BLE improvement.
Figure 10:
FIGS. 10-21 are screen shots from one embodiment of the invention (PLC & BLE improvement) as shown on the screen of a mobile computing device or Smart Phone.
Figure 11:
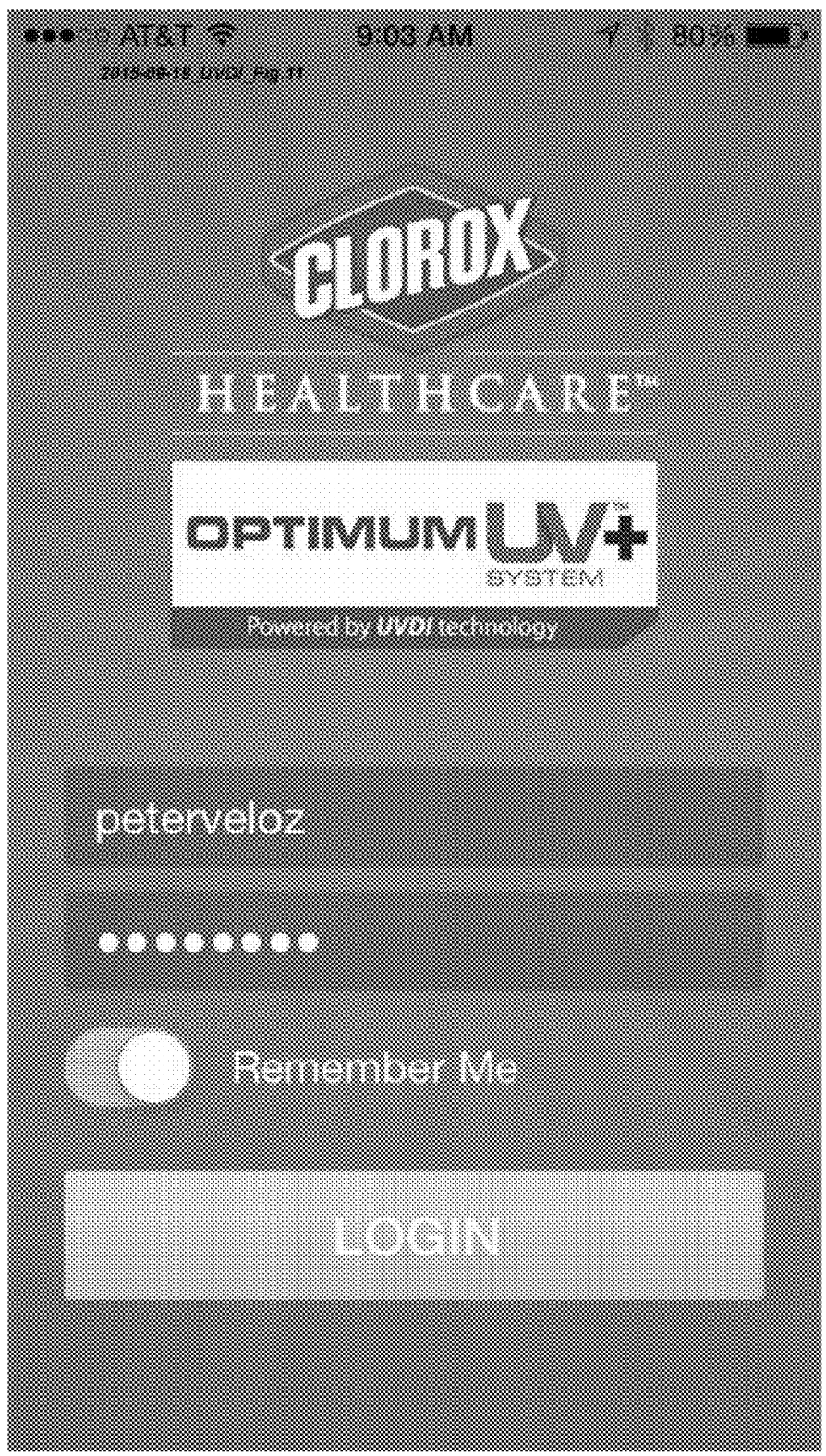
Figure 12:
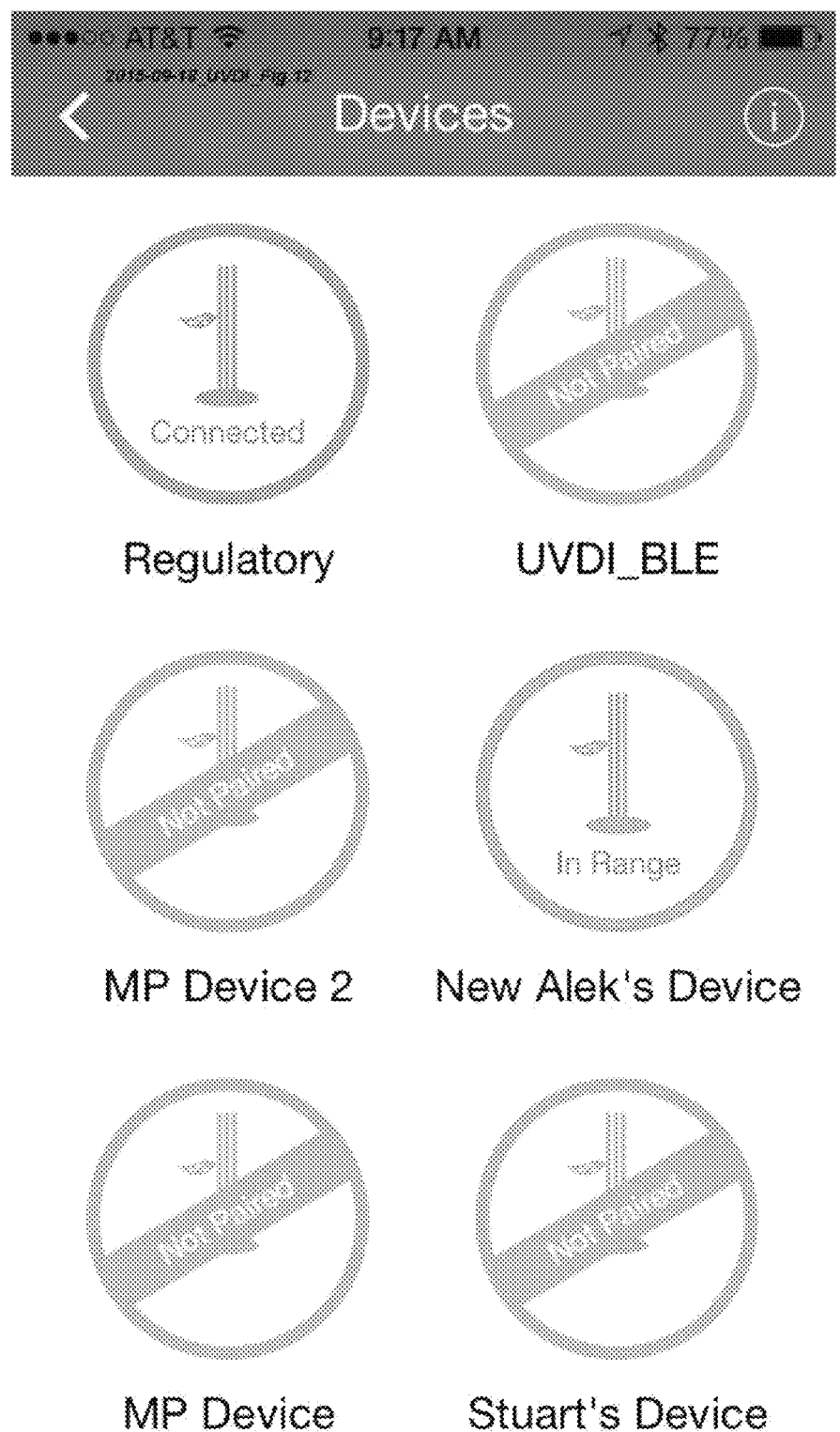
Figure 13:
Figure 14:
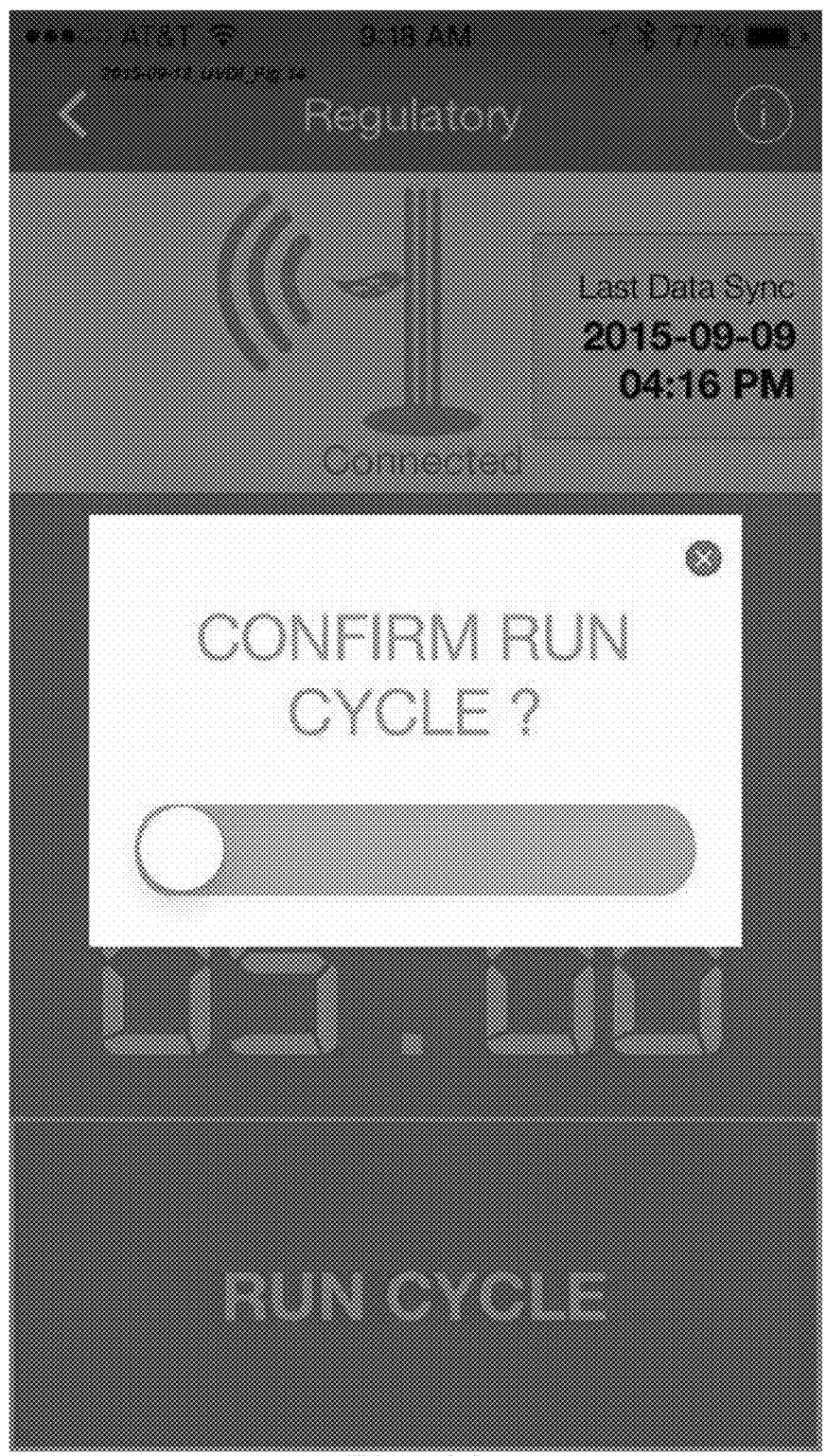
Figure 15:
Figure 16:
Figure 17:
Figure 18:
Figure 19:
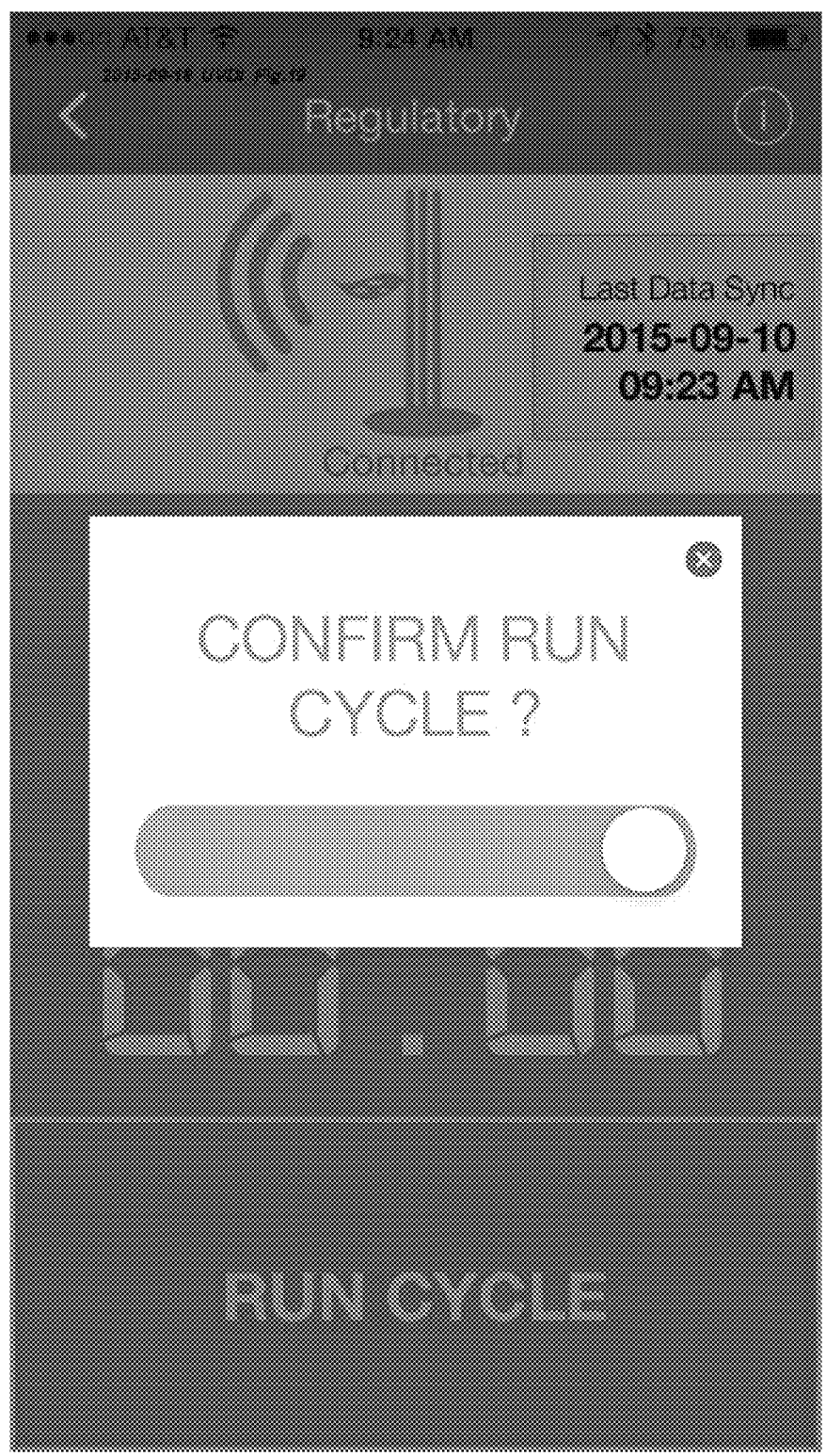
Figure 20:
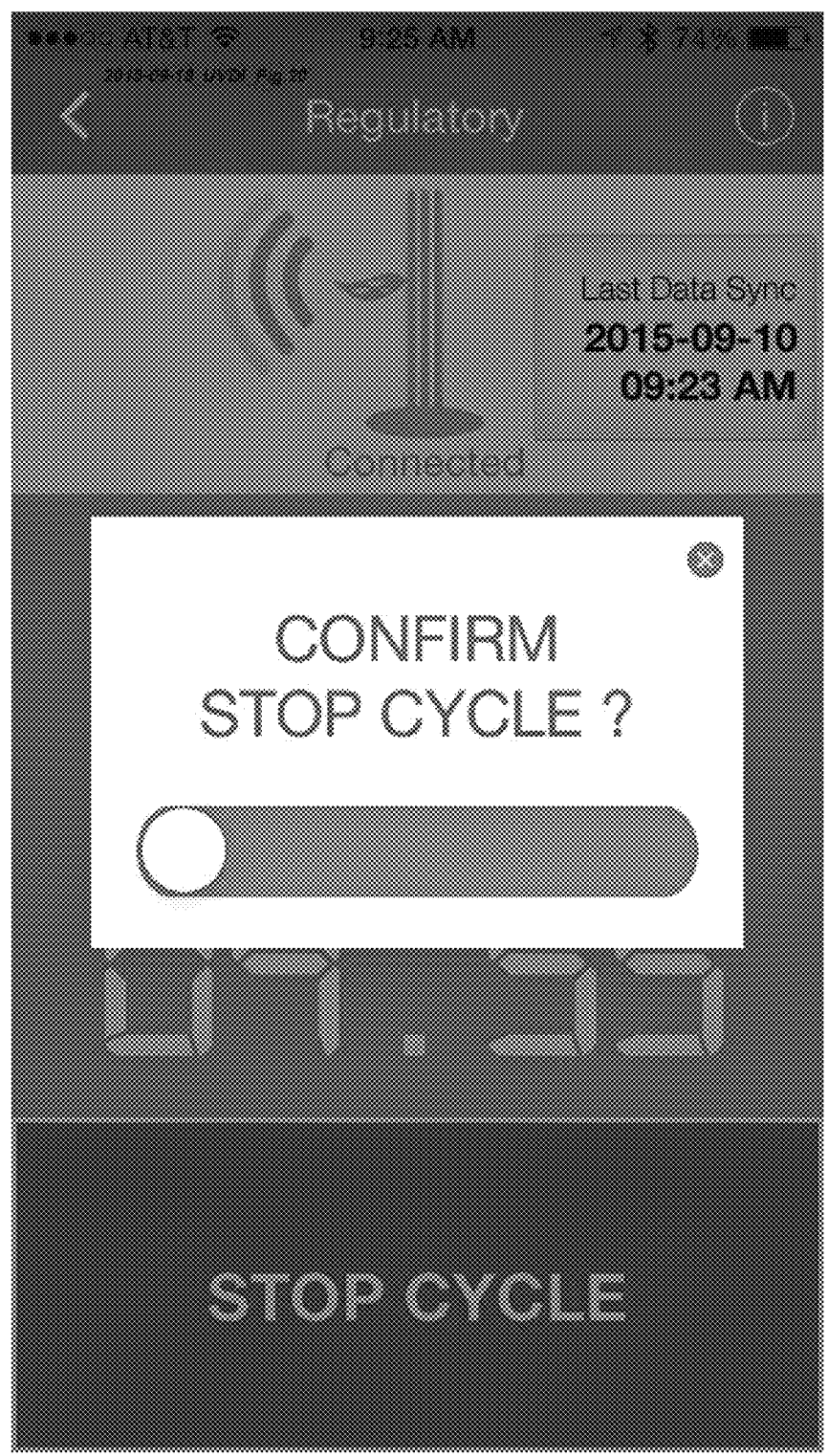
Figure 21:

Additional connectivity can be provided through traditional wireless means such as WiFi or Bluetooth, but WiFi is generally crowded in a hospital or healthcare setting and also poses additional security complications; Bluetooth is range limited and requires too much energy. Looking at FIG. 9, the UV device employs the PLC with BLE to be able to communicate with the user's smartphone or tablet.

The single board computer can have multiple digital inputs for cycle monitoring and at least one digital output for the master shut-off. The BLE module/single board computer can have additional analog outputs to enable BLE connectivity of remote sensors to the PLC/HMI.

There is also connectivity for remote UV sensors, including without limitation: a wireless UV-C sensor. For example, this sensor can be placed at certain locations in the hospital room in close proximity to the UV device and will read the device output at that location. Through the BLE connection, the sensor is enabled and allows the sensor reading to be sent wirelessly (BLE) to the smart device such as tablet or phone, which is located outside the room, either though the single board computer or directly to the smart device. Sending the sensor information to the single board computer will provide the device the necessary input for determining the appropriate disinfection cycle time. It will also provide the user useful data to determine the appropriate placement of the device in the room as well as the appropriate cycle time.

Connectivity can also be established for room identification sensors. Specific room number identification can be programmed into a BLE beacon placed in the room. Through the BLE connection, the room information from the beacon is sent wirelessly to the PLC/HMI via the single board computer to record the room information. This functionality will eliminate the need for the user to enter the room number. Alternatively, the BLE beacons can transmit the room information directly to the smart device outside the room using the BLE connectivity.

There are warning signs and signals to provide visual or auditory indicators of the status of a disinfection cycle into the protective case (cover) for the device. The protective case can serve as the warning sign to prevent people from entering the room when the device is in operation. A visual indicator outside the room would let people know whether the disinfection cycle has been completed and when it is safe to go back inside the room and retrieve the UV device. The visual indicator can alternatively be integrated into a warning sign or device protective case placed outside the room when the disinfection cycle is in progress in the room. A smart device such as a smartphone, tablet or IPod Touch can be installed on the protective case or warning sign and serves as a visual indication of the status of a disinfection cycle. The smart device receives status of the disinfection cycle from the device via the BLE connectivity developed above; additionally, the BLE connectivity allows the smart device to receive data from the UV device.

Alternatively, the protective case or warning sign can house a BLE module instead of the smart device. This module has the connectivity, necessary processor strength and necessary I/Os. Alternatively, the BLE module (interface) can be free-standing or mountable outside the room. The module can have multiple outputs for the lights that will be triggered and at least one input for the master shut off button. The module can communicate with the PLC/HMI of the device and is easy to interpret. The module can have up to three light indicators to indicate the cycle status (e.g. red: cycle is on; yellow: cycle interrupted; green: cycle complete).

A robust battery power supply is to be provided that can last upwards of 1-3 years and be exchanged easily.

This invention also provides a remote cut off functionality, which will cut-off all power to the UV device via radio frequency or BLE, bypassing the PLC. This would serve as a master shut off of the UV system as a safety precaution, if needed.

The smart device or BLE module communicates to the PLC through a single board computer (SBC). The SBC is connected through hardwire to the PLC and HMI using the Ethernet port on the PLC. The SBC may also communicate with a wireless router or another internet connected device.

The single board computer (SBC) communicates with the PLC and HMI on a regular basis to establish the current status of the PLC and HMI, using commands specific to the PLC and HMI. This communication may also happen in response to a specific request from the smart device. This status and/or associated data is converted to a standard format by the SBC.

The mobile computing device or smart device may from time to time connect to the SBC using BLE in response to user requests. The SBC can convert these into requests to the HMI and/or PLC to initiate requested actions or to return logged data or status.

The inventors believe that the novel and non-obvious portions of this invention include:
1. Bluetooth or Bluetooth Low Energy control of PLC/HMI from Phone app;
2. Standardised BLE interface to PLC/HMI via translation layer [commands in JSON actioned via proprietary HMI/PLC commands]; in addition, it is possible to swap out to other HMI/PLC and keep the app the same;
3. BLE to Ethernet via translation layer;
4. Timer synchronization (i.e. free running timer on app).
5. Ability for the SBC to receive and record information from remote sensors (BLE beacons) and upload to PLC and HMI.

Wireless Connectivity to/from the UV Disinfection Device

The improvement to the above invention involves appropriate hardware & firmware solution that can be integrated with the PLC (programmable logic controller) and HMI system (human machine interface) on the device in order to communicate with the UV device wirelessly and transmit the data to a UVDI controlled Cloud based server. The hardware and software module presented enables access to the operating status of the UV device and the transfer of data (typically, a .csv file) for further processing.

Wireless connectivity is to be provided preferably via BLE (Bluetooth Low Energy) or another low energy wireless communication system. The data should be able to be transmitted via BLE to a smart device (tablet or smartphone) enabled by a mobile software application ("app"). This app will serve as a gateway to view and move the data file to a Cloud based server from the smart device.

Additional connectivity can be provided through WiFi. Different from the purpose to provide data transmission, this WiFi connectivity can provide the factory access to the device remotely on a scheduled and less frequent basis. The goal is for some diagnostic information to be gained by the factory and maintenance in the form of uploading necessary patches or updates to the PLC/HMI to be able to occur.

This invention improvement presents one preferred embodiment of a module with appropriate hardware and firmware that will provide both BLE and WiFi connectivity to the PLC as well as the HMI. Without being limiting, one preferred method of connection to the PLC/HMI is via the Ethernet port on the UV device.

There is used a single board computer (SBC) that has Ethernet, Bluetooth LE, and Wi-Fi interfaces. The board can support a web browser to accept the web server page provided by the IDEC PLC model FC5A-D12K1E and HMI display model HG2G-5FT22TF-B (examples only and not intended to be limiting).

The single board computer in the device can be available as an IP-connected node on the Wi-Fi network to which it is connected. Data can be accessed at other locations subject to appropriate set up of firewalls, access control etc. within the network to which it attaches. The network setup can regulate access and can vary due to the location or environment; information should be encrypted.

Any connected device will be able to display the web page from the PLC and HMI over the Wi-Fi interface.

A smartphone or other wireless computing device can display the web page from the HMI display over the Bluetooth LE interface, and will display the web page from the PLC and HMI over the Wi-Fi interface. It is not necessary for both web pages to be accessed at the same time.

The firmware allows the operator to switch the wireless connectivity from BLE transmission to Wi-Fi. The PLC will have a digital output that can be connected to a digital input on the single board computer to turn the Wi-Fi: on and off.

Data download: the HMI can log event data internally, which can be periodically downloaded through a Bluetooth LE connected device, such as a smart phone. For example, the PLC manufacturer (IDEC) provides Windows software called "Data Downloader," which can download this data into a PC; there can also be an application that can download this data to the single board computer and make it available to Bluetooth LE connected devices.

Connectivity (I/O) for cycle status notification: the single board computer can have multiple or 3 digital inputs to provide the status of the UV Device and 1 digital output for the shut-off switch. This information should be retrievable by the smart device through BLE interface. This should include the necessary firmware to enable this connectivity.

Connectivity for remote sensors: the BLE module/single board computer should have multiple additional analog outputs to enable BLE connectivity of remote sensors.

One preferred and non-limiting example of the System Architecture includes: the central processor in the system is a single board computer (SBC) from Technologic Systems (TS-7680). Specific to this task, the SBC is equipped with: 2× network ports; 1× USB host port; 2× relay outputs; Flexible PSU; Integrated WiFi/BLE module; and Optional external BLE antenna.

The SBC is connected to the HMI and PLC, which comprise the UVDI system using Ethernet. It communicates with the HMI and PLC over Ethernet.

Certain information described below is presented out to a mobile computing device, such as a tablet or a Smartphone over the BLE interface. In addition, the SBC may revert to a WiFi connection for the transfer of data. A relay on the SBC controls the "emergency stop" to the UVDI application and may be viewed as a safety relay.

Communication with the PLC and HMI is achieved over the Ethernet interfaces using protocols, which are specific to the IDEC PLC and HMI's used. Internal registers, motor settings can be read/written to in order to determine the state of the system. In addition, log files may be recovered from the HMI in CSV format, again subject to the IDEC proprietary protocols.

At the simplest level, the cellphone will connect to the SBC using BLE. The SBC will advertise a GATT service and this will facilitate two way communication using a "serial line" type methodology.

In one preferred embodiment, the SBC will be commanded to open a WiFi line—either to the cellphone or to another service. This may be used to provide a maintenance channel to the SBC/HMI.

In this mode, the SBC will allow: (1) Direct communication to the PLC and HMI (as a gateway), enabling the use of standard IDEC tools; (2) Command to be given to upload log files directly to UVDI servers.

Communication between the smart phone and the SBC, over GATT (GATT is an acronym for the Generic Attribute Profile and defines the way that two Bluetooth LE devices transfer data back and forth using concepts called Services and Characteristics), can be in JSON format. This allows for flexibility and future expansion.

Possible Commands: Start Cycle; Stop Cycle; Emergency Stop; Return Cycle status; Return Cycle data; Countdown timer; Cycle time timer; Lamp status and alerts; and Room information.

One Possible Embodiment

Each transaction can be initiated from the cellphone and takes the following format:
{
  "Transaction ID": 1,
  "Command": "command"
}
Transaction ID is a monotonically increasing number. If the SBC receives a number that is out of sequence an error is reported and the application halts. "command" is per the command list below, and additional data may be included.

Each transaction is responded to by the SBC, either as an acknowledgement or including the requested data, in the following format:
{
  "Transaction ID": 1
  "Response": "response"
}
Response is One of:
"OK"—acknowledgement of action.
"Error"—error occurred. An additional field "Error number": describes the error number (TBD) and "Error text": describes the error in textual format. Note that a non-sequential transaction ID is an error.
Commands are:
"Start Cycle"—start a treatment cycle.
"Stop Cycle"—stop a treatment cycle
"Emergency Stop"—open the safety relay
"Cycle status"—return the status of a cycle. Data returned from the SBC is:
  "Status": "Running"
  "Status": "Interrupted"
  "Status": "Complete"
"Cycle Data"—return cycle data. Note that this is a CSV file which is not specifically converted to JSON objects—but it is embedded within an array. Newline characters are escaped and treated as special characters to ease conversion.
Data Returned is (in Simplified Form)
  "Data": ["Room", "Date", "/n", "1001", "12/13/2015", "/n", "1002", "12/14/2015"]
  JSON can be defined as JavaScript Object Notation and is an open standard format that uses human-readable text to transmit data objects consisting of attribute-value pairs.

Bluetooth Low Energy (BLE):
From the webpage: http://www.bluetooth.com/Pages/low-energy-tech-info.aspx, which is incorporated by reference.
"The Low Energy Technology Behind Bluetooth Smart
Thanks to its innovative design, Bluetooth® Smart technology consumes only a fraction of the power of Classic Bluetooth radios. Bluetooth Smart extends the use of Bluetooth wireless technology to devices that are powered by small, coin-cell batteries such as watches and toys. Other devices such as sports & fitness, health care, keyboards and mice, beacons, wearables and entertainment devices are enhanced by this version of the technology. In many cases, it makes it possible to operate these devices for more than a year without recharging.

As with previous versions of the specification, the range of the radio may be optimized according to application. The majority of Bluetooth devices on the market today include the basic 30 foot, or 10 meter, range of the Classic Bluetooth radio, but there is no limit imposed by the Specification. With Bluetooth Smart, manufacturers may choose to optimize range to 200 feet and beyond, particularly for in-home sensor applications where longer range is a necessity.

Bluetooth Smart features provides:
  Ultra-low peak, average and idle mode power consumption
  Ability to run for years on standard coin-cell batteries
  Lower implementation costs
  Multi-vendor interoperability
  Enhanced range
  This enhancement to the Bluetooth Core Specification allows two types of implementation, dual-mode and single-mode. In a dual-mode implementation, Bluetooth low energy functionality is integrated into an existing Classic Bluetooth controller. The resulting architecture shares much of Classic Bluetooth technology's existing radio and functionality resulting in a minimal cost increase compared to Classic Bluetooth technology. Additionally, manufacturers can use current Classic Bluetooth technology (Bluetooth v2.1+EDR or Bluetooth v3.0+HS) chips with the new low energy stack, enhancing the development of Classic Bluetooth enabled devices with new capabilities.

Single-mode chips, which will enable highly integrated and compact devices, will feature a lightweight Link Layer providing ultra-low power idle mode operation, simple device discovery, and reliable point-to-multipoint data transfer with advanced power-save and secure encrypted connections at the lowest possible cost. The Link Layer in these controllers will enable Internet connected sensors to schedule Bluetooth low energy traffic between Bluetooth transmissions.

Registered members of the Bluetooth SIG can access in-depth technical information about Bluetooth low energy technology. (You must be on-line and logged in as a registered member of the SIG to access this link). If you're not a member, register today.
Technical Details
  Data Transfers—Bluetooth Smart (low energy) supports very short data packets (8 octet minimum up to 27 octets maximum) that are transferred at 1 Mbps. All connections use advanced sniff-sub rating to achieve ultra low duty cycles
  Frequency Hopping—Bluetooth Smart (low energy) uses the adaptive frequency hopping common to all versions of Bluetooth technology to minimize interference from other technologies in the 2.4 GHz ISM Band. Efficient multi-path benefits increase the link budgets and range Host Control—Bluetooth Smart (low energy) places a significant amount of intelligence in the controller, which allows the host to sleep for longer periods of time and be woken up by the controller only when the host needs to perform some action. This allows for the greatest current savings since the host is assumed to consume more power than the controller Latency—Bluetooth Smart (low energy) can support connection setup and data transfer as low as 3 ms, allowing an application to form a connection and then transfer authenticated data in few milliseconds for a short communication burst before quickly tearing down the connection Range—Increased modulation index provides a possible range for Bluetooth Smart (low energy) of over 100 meters Robustness—Bluetooth Smart (low energy) uses a strong 24 bit CRC on all packets ensuring the maximum robustness against interference Strong Security—Full AES-128 encryption using CCM to provide strong encryption and authentication of data packets Topology—Bluetooth Smart (low energy) uses a 32 bit access address on every packet for each slave, allowing billions of devices to be connected. The technology is optimized for one-to-one connections while allowing one-to-many connections using a star topology."

This invention refers to computing programs, applications or software, which are all synonymous and are used interchangeably. This invention can be applied to any computing device that is connected to a communication network or the Internet via wired or wireless connection.

The embodiments of the invention may be implemented by a processor-based computer system. The system includes a database for receiving and storing information from users and application software for users and displaying feedback information.

In accordance with the present invention, computer system operates to execute the functionality for server component. Computer system includes a processor and memory and disk storage. Memory stores computer program instructions and data. Processor executes the program instructions or software, and processes the data stored in memory. Disk storage stores data to be transferred to and from memory. Note that disk storage can be used to store data that is typically stored in the database.

All these elements are interconnected by one or more buses, which allow data to be intercommunicated between the elements. Note that memory is accessible by processor over a bus and includes: an operating system, a program partition and a data partition. The program partition stores and allows execution by processor of program instructions that implement the functions of each respective system described herein. The data partition is accessible by processor and stores data used during the execution of program instructions.

For purposes of this application, memory and disk are machine readable mediums and could include any medium capable of storing instructions adapted to be executed by a processor. Some examples of such media include, but are not limited to, read-only memory (ROM), random-access memory (RAM), programmable ROM, erasable programmable ROM, electronically erasable programmable ROM, dynamic RAM, magnetic disk (e.g., floppy disk and hard drive), optical disk (e.g., CD-ROM), optical fiber, electrical signals, light wave signals, radio-frequency (RF) signals and any other device or signal that can store digital information.

In one embodiment, the instructions are stored on the medium in a compressed and/or encrypted format. As used herein, the phrase "adapted to be executed by a processor" is meant to encompass instructions stored in a compressed and/or encrypted format, as well as instructions that have to be compiled or installed by an installer before being executed by the processor. Further, system may contain various combinations of machine readable storage devices, which are accessible by processor and which are capable of storing a combination of computer program instructions and data.

A computer system also includes a network interface. Network interface may be any suitable means for controlling communication signals between network devices using a desired set of communications protocols, services and operating procedures. Communication protocols are layered, which is also referred to as a protocol stack, as represented by operating system, a CBE-communication layer, and a Transport Control Protocol/Internet Protocol (TCP/IP) layer. Network interface may also include connectors for connecting interface with a suitable communications medium. Those skilled in the art will understand that network interface may receive communication signals over any suitable medium such as twisted-pair wire, co-axial cable, fiber optics, radio-frequencies, and so forth.

A typical computer system includes a processor, a memory, disk storage, a network interface, and a protocol stack having a CBE-communication layer and a TCP/IP layer. These elements operate in a manner similar to the corresponding elements for computer system.

An apparatus for disinfection of air and surfaces, comprising: a UV lamp having a mercury amalgam spot; a power source; a conduit body, which has at least one hole that is located near the mercury spot of the UV lamp; and an air moving device, which delivers air through the conduit body in a first direction; and the at least one hole directs the air in a second direction and near the mercury spot of the UV lamp;

the apparatus further comprises: a programmable logic controller (PLC); a single board computer (SBC); and a human machine interface (HMI);

a wireless communication controller communicates to the programmable logic controller through the single board computer;

the single board computer is connected through hardwire to the programmable logic controller and the human machine interface using an Ethernet port on the programmable logic controller or a serial port or USB port or through a wireless router or an internet connected device;

whereby the air moving device provides cooling to alter the temperature near the mercury amalgam spot of the UV lamp and the wireless communication controller controls the apparatus;

the wireless communication controller can use Bluetooth Low Energy (BLE), low energy wireless communication or WiFi technology to communicate with the programmable logic controller; and the single board computer has Ethernet, Bluetooth Low Energy and WiFi interfaces;

at least one remote UV sensors is wirelessly connected to said apparatus and said wireless communication controller; the wireless communication controller is a Smart Phone, tablet, handheld PC or mobile computing device; the computing device or the single board computer communicates with the programmable logic controller and the human machine interface, and the computing device or the single board computer uses commands specific to the programmable logic controller and the human machine interface; the apparatus can transmit data to an Internet based server; and the wireless controller can control and display the operating status of the UV apparatus.

We claim:

1. An apparatus for disinfection of air and surfaces, comprising:
   A UV lamp having a mercury amalgam spot;
   A power source;
   A conduit body, which has at least one hole that is located near the mercury spot of the UV lamp; and
   An air moving device, which delivers air through the conduit body in a first direction; and the at least one hole directs the air in a second direction and near the mercury spot of the UV lamp;
   the apparatus further comprises:
      a programmable logic controller (PLC);
      a computing device of the apparatus; and
      a human machine interface (HMI);
   a wireless communication controller communicates to the programmable logic controller through the computing device;
   the computing device of the apparatus is connected through hardwire to the programmable logic controller and the human machine interface using an Ethernet port on the programmable logic controller or a serial port or USB port or through a wireless router or an internet connected device;
   whereby the air moving device provides cooling to alter the temperature near the mercury amalgam spot of the UV lamp, and the wireless communication controller controls the apparatus.

2. The apparatus of claim 1, wherein the wireless communication controller uses Bluetooth Low Energy (BLE), low energy wireless communication or WiFi technology to communicate with the programmable logic controller; and the computing device of the apparatus has Ethernet, Bluetooth Low Energy and WiFi interfaces.

3. The apparatus of claim 1, wherein at least one remote UV sensors is wirelessly connected to said apparatus and said wireless communication controller.

4. The apparatus of claim 1, wherein the wireless communication controller is a Smart Phone, a tablet, a handheld PC or a mobile computing device.

5. The apparatus of claim 1, wherein the computing device of the apparatus communicates with the programmable logic controller and the human machine interface, and the computing device of the apparatus uses commands specific to the programmable logic controller and the human machine interface.

6. The apparatus of claim 1, wherein the apparatus transmits data to an Internet based server.

7. The apparatus of claim 1, wherein the wireless controller controls and displays the operating status of the UV apparatus.

8. The apparatus of claim 1, wherein the computing device of the apparatus is a single board computer (SBC).

* * * * *